(12) United States Patent
Lee

(10) Patent No.: US 10,168,280 B2
(45) Date of Patent: Jan. 1, 2019

(54) AUTHENTICATION STRUCTURE AND AUTHENTICATION METHOD USING THE SAME

(71) Applicant: SAMSUNG ELECTRONICS CO., LTD., Suwon-si (KR)

(72) Inventor: Jaesoong Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/458,187

(22) Filed: Mar. 14, 2017

(65) Prior Publication Data

US 2018/0059018 A1 Mar. 1, 2018

(30) Foreign Application Priority Data

Aug. 23, 2016 (KR) .......................... 10-2016-0106993

(51) Int. Cl.
| | |
|---|---|
| *G01N 21/55* | (2014.01) |
| *G01N 21/47* | (2006.01) |
| *G01N 21/552* | (2014.01) |
| *G07D 7/12* | (2016.01) |
| *G02B 6/42* | (2006.01) |
| *H04W 12/06* | (2009.01) |

(52) U.S. Cl.
CPC ....... *G01N 21/4788* (2013.01); *G01N 21/553* (2013.01); *G02B 6/4214* (2013.01); *G07D 7/12* (2013.01); *H04W 12/06* (2013.01); *G01N 2021/479* (2013.01); *G01N 2021/4792* (2013.01); *G01N 2201/0873* (2013.01)

(58) Field of Classification Search
CPC ............ G01N 21/4788; G01N 21/552; G01N 21/553; G01N 2021/479; G01N 2021/4792; G01N 2201/0873; G07D 7/12; G02B 27/48; G02B 6/122; G02B 6/0043; G02B 6/1226; F21V 8/00
See application file for complete search history.

(56) References Cited

U.S. PATENT DOCUMENTS

| | | |
|---|---|---|
| 2008/0141364 A1 | 6/2008 | Skoric et al. |
| 2009/0153841 A1 | 6/2009 | Ophey et al. |
| 2016/0103065 A1* | 4/2016 | Lee ...................... G01N 21/553 356/445 |

FOREIGN PATENT DOCUMENTS

| | | |
|---|---|---|
| KR | 1020070114269 A | 11/2007 |
| WO | 2006021911 A1 | 3/2006 |

OTHER PUBLICATIONS

Gao et al: "Exploiting PUF Unreliability to Secure Wireless Sensing", Cryptology ePrint Archive: Report 2015/1240 (Dec. 2015), pp. 1-10, (10 pages total).

(Continued)

*Primary Examiner* — Jamil Ahmed
(74) *Attorney, Agent, or Firm* — Sughrue Mion, PLLC

(57) ABSTRACT

An authentication structure and an authenticating method using the same are provided. The authentication structure includes a plurality of input couplers that generate surface plasmons by being selectively coupled to lights because the plurality of input couplers are different in terms of at least one of a geometric structure and an arrangement, and an output coupler that outputs a speckle pattern based on the surface plasmons.

19 Claims, 11 Drawing Sheets

(56) References Cited

OTHER PUBLICATIONS

Guarjardo et al: "Brand and IP Protection with Physical Unclonable Functions", 2008 IEEE International Symposium on Circuits and Systems, pp. 3186-3189 (May 18-21, 2008), (4 pages total).
P. Tuyls, B. Skoric: "Secret Key Generation from Classical Physics Physical Uncloneable Functions"; Amlware Hardware Technology Drivers of Ambient Intelligence vol. 5 of the series Philips Research, p. 421-447 (2006), (20 pages total).
Ravikanth Pappu et al., "Physical One-Way Functions", Science, Sep. 20, 2002, vol. 297, No. 5589, pp. 2026-2030. (6 pages total).

\* cited by examiner

AUTHENTICATION STRUCTURE AND AUTHENTICATION METHOD USING THE SAME

CROSS-REFERENCE TO RELATED APPLICATION

This application claims priority from Korean Patent Application No. 10-2016-0106993, filed on Aug. 23, 2016 in the Korean Intellectual Property Office, the disclosure of which is incorporated herein in by reference its entirety.

BACKGROUND

1. Field

Apparatuses and method consistent with exemplary embodiments relate to authentication structures for authenticating objects and authentication methods using the authentication structures.

2. Description of the Related Art

A physical unclonable function (PUF) may be used for security purposes. For example, when a PUF is applied to a device (or a product), such as a smart card, a memory stick, a storage medium, or a chip, it may be practically impossible to duplicate the device incorporating the PUF.

A PUF is based on the concept that a slight difference that is caused during a process is used as an identity or identifier of an individual device. For example, when light is emitted to a token that is formed by randomly distributing glass beads, a unique pattern is created. Because tokens are generally formed by distributing glass beads, the glass beads are randomly arranged in all of the tokens, and thus it is physically impossible to form the same token. Different patterns are created from tokens, and thus unique identities of the tokens or products including the tokens are established, like human fingerprints. A process of verifying identity, for example by using the token or human fingerprint, is referred to as authentication.

However, when authenticating a token that is formed by distributing glass beads, an image unfortunately varies according to a direction in which light is emitted to the token, a position of the token, and a position of a detector. Also, because the token has a large size, a relatively bulky measurement system is used for authentication. Accordingly, it is difficult to popularize or commercialize authentication using the PUF.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide authentication structures (security structures) that may be used to authenticate objects.

Further, one or more exemplary embodiments provide authentication structures capable of outputting various speckle patterns according to the characteristics of incident light.

According to an aspect of an exemplary embodiment, there is provided an authentication structure including: a first input coupler oriented in a first direction and configured to generate first surface plasmons from first light having first light characteristics from among incident light; input coupler oriented in a second direction different from the first direction and configured to generate second surface plasmons from second light having second light characteristics from among the incident light; and an output coupler spaced apart from the first and second input couplers and configured to output a speckle pattern based on at least one of the first and second surface plasmons.

The first light and the second light may be different in terms of at least one of a polarization and a wavelength.

An included angle between the first direction and the second direction may be less than 180°.

The first direction and the second direction may intersect at 90°.

The first input coupler and the second input coupler may be spaced apart from each other.

The first input coupler and the second input coupler partially may overlap each other.

A length of the first input coupler may be different from a length of the second input coupler.

The first input coupler may be coupled to light having a polarization characteristic that is parallel to the first direction.

The output coupler may output different speckle patterns according to the characteristics of the first and second surface plasmons.

The first output coupler may output a first speckle pattern based on the first surface plasmons, output a second speckle pattern based on the second surface plasmons, and output a third speckle pattern based on the first and second surface plasmons.

The authentication structure further includes a waveguide configured to transmit at least one of the first and second surface plasmons to the output coupler.

The authentication structure may include a layer structure that is a single-layer structure or a multi-layer structure, the first and second input couplers are provided in a first area of the layer structure, and the output coupler is provided in a second area of the layer structure.

The first area is at a first distal end of the layer structure and the second area may be at a second distal end of the layer structure.

The first and second input couplers may comprise at least one of a slit and a slot disposed in the first area of the layer structure.

The output coupler may comprise a plurality of optical scatterers disposed in the second area of the layer structure.

Each of the plurality of optical scatterers may has a nanoscale size or a microscale size.

At least one of the plurality of optical scatterers may comprise a slit, a slot, a spherical element, or a rod-type element.

The layer structure may comprise a metal film.

According to an aspect of another exemplary embodiment, is provided a method of authenticating an authentication structure including a plurality of input couplers that have different geometric structures or arrangements from each other and an output coupler. The method may include emitting light to the plurality of input couplers; and generating surface plasmons by the plurality of input couplers being selectively coupled to lights having different light characteristics among the emitted light; and detecting a speckle pattern output by the output coupler based on the surface plasmons.

The speckle pattern may vary depending on the light characteristics.

According to an aspect of another exemplary embodiment, there is provided an authentication device including: a light source configured to emit, to a layer structure, a first laser beam having a first polarization and a second laser beam having a second polarization different from the first polarization; a first input coupler that is disposed on the layer structure in a first direction and generates first surface plasmons in response to the first laser beam being incident on the input coupler; a second input coupler that is disposed on the layer structure in a second direction different from the first direction and generates second surface plasmons in response to the second laser beam being incident on the input coupler; and an output coupler that is disposed on the layer structure, generates a first speckle pattern in response to the first surface plasmons traveling along the layer structure and reaching the output coupler, and generates a second speckle pattern different from the first speck pattern in response to the second surface plasmons traveling along the layer structure and reaching the output coupler.

DETAILED DESCRIPTION

Figure 1A:
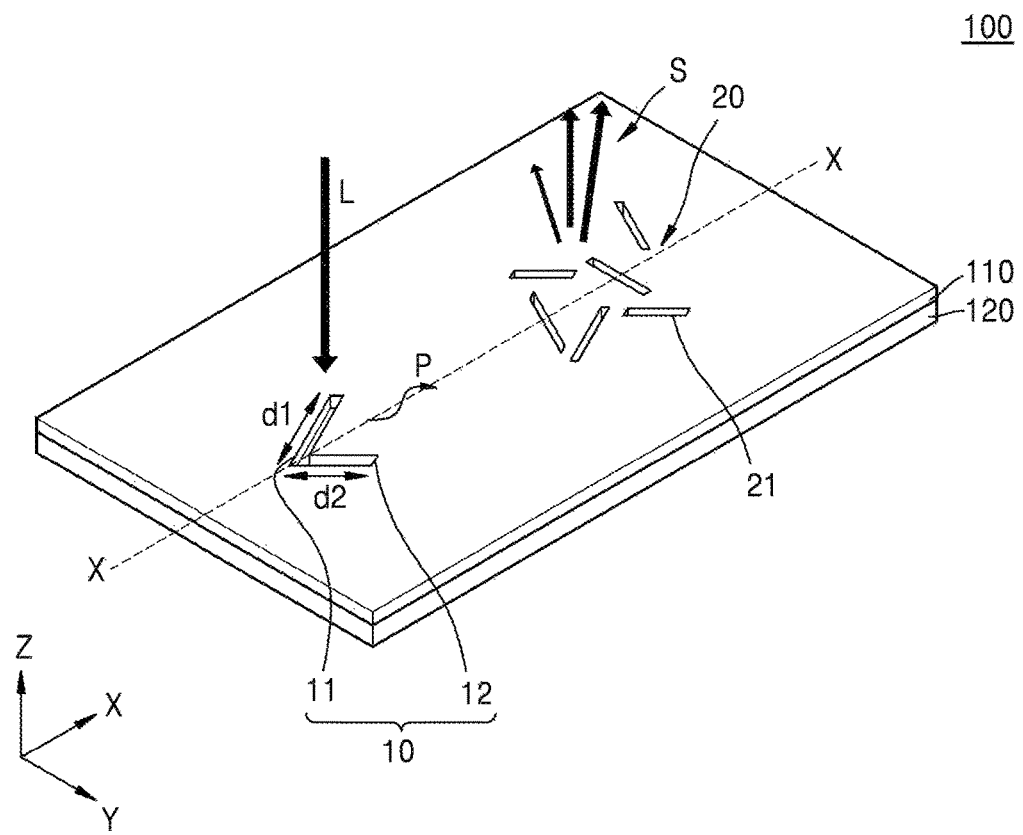
FIG. 1A is a perspective view of an authentication structure according to exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Expressions such as "at least one of," when preceding a list of elements, modify the entire list of elements and do not modify the individual elements of the list.

Figure 1B:
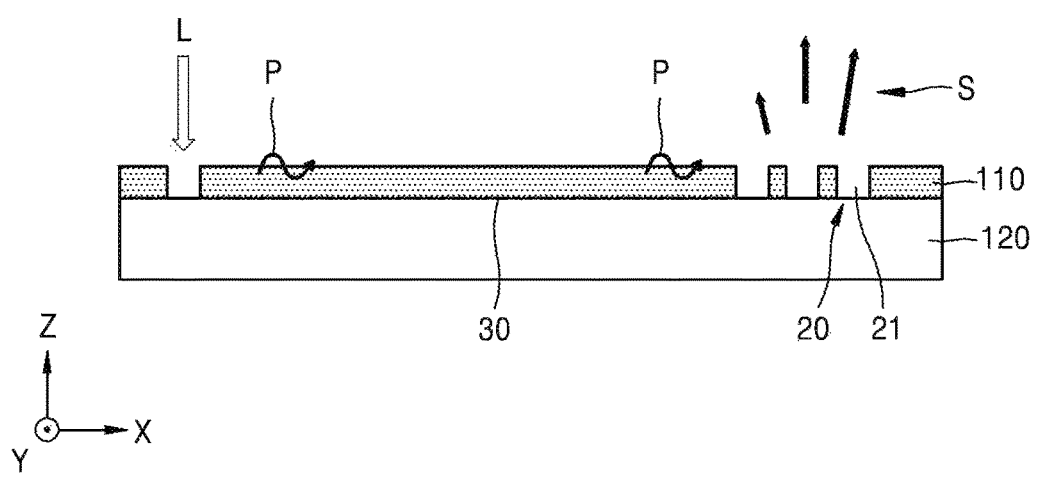
FIG. 1B is a cross-sectional view of the authentication structure of FIG. 1A.

FIG. 1A is a perspective view of an authentication structure 100 according to an exemplary embodiment, and FIG. 1B is a cross-sectional view of the authentication structure 100. The authentication structure 100 may be referred to as an authentication token, a physical unclonable function (PUF) token, or a PUF structure. Also, the authentication structure 100 may be referred to as an optical authentication structure 100. Also, the authentication structure 100 may be referred to as a security device.

The authentication structure 100 may be disposed on an object and may be inserted into the object. The object is a device, mechanism, or product, and the authentication structure 100 may be applied to the object for security purposes.

Referring to FIGS. 1A and 1B, the authentication structure 100 may be configured to output a speckle pattern S produced by surface plasmons P. An identity of the object including the authentication structure 100 may be verified by detecting the speckle pattern S.

The authentication structure 100 may include an input coupler 10 that generates the surface plasmons P using incident light L, and an output coupler 20 that generates and outputs the speckle pattern S produced by the surface plasmons P. The authentication structure 100 may also include a waveguide 30 that transmits (or guides) the surface plasmons P generated by the input coupler 10 to the output coupler 20. The waveguide 30 may be referred to as an optical waveguide, and may be disposed between the input coupler 10 and the output coupler 20. The incident light L may be coherent light. For example, the incident light L may be laser light.

The input coupler 10 may include a slit and/or a slot. The terms 'slit' and 'slot' may each refer to a long narrow groove or opening. Lengthwise directions of first and second input couplers 11 and 12 that constitute the input coupler 10 may mean the directions of the longest lengths of slits or slots. The slit and the slot used herein may be distinguished from each other by a size and a depth of a groove. For example, 'slit' may refer to a groove having a larger size and a greater depth than those of the 'slot'. However, the size and shape of the slit and the slot are not limited thereto and the terms slit and the slot may be interchangeably used.

The slit and the slot are an exemplary structure that may be included in the input coupler 10. A configuration or a structure of the input coupler 10 may be modified in various ways. Any desired structure that may generate the surface plasmons P by using the incident light L may be used for the input coupler 10. Also, when the input coupler 10 has an opening or a groove, a material may be filled in the opening or the groove.

Because the input coupler 10 includes a plurality of sub input couplers different from each other in terms of at least one of a geometric structure and an arrangement, the plurality of sub input couplers may be differently coupled to a plurality of lights having different light characteristics, respectively.

For example, the input coupler 10 may include a first input coupler 11 oriented in a first direction d1 and capable of generating first surface plasmons P1 from first light L1 included in incident light L, and a second input coupler 12 oriented in a second direction d2 different from the first direction d1 and capable of generating second surface plasmons P2 from second light L2 included in the incident light L.

The first light L1 and the second light L2 may have different optical characteristics. The light characteristics used herein may include at least one of a polarization and a wavelength. For example, the first light L1 may be light having a first polarization (for example, a P polarization), and the second light L2 may be light having a second polarization (for example, a S polarization). Alternatively, the first light L1 may be light in a first central wavelength band, and the second light L2 may be light in a second central wavelength band. The first light L1 may have a single light characteristic that is different from that of the second light L2 or may have a plurality of light characteristics that are different from those of the second light L2. For example, the first light L1 may be light having a P polarization in a first wavelength band, and the second light L2 may be light having an S polarization in a second wavelength band.

The first input coupler 11 may be oriented in the first direction d1, and the second input coupler 12 may be oriented in the second direction d2. Being oriented in the first direction d1 may mean the lengthwise direction of the first input coupler 11 being parallel to the first direction d1, and being oriented in the second direction d2 may mean the lengthwise direction of the second input coupler 12 being parallel to the second direction d2. Thus, the first input coupler 11 may be coupled to light having polarization characteristics parallel to the first direction d1, and the second input coupler 12 may be coupled to light having polarization characteristics parallel to the second direction d2.

An included angle between the first and second directions d1 and d2 may be less than 180°. For example, the first direction d1 and the second direction d2 may intersect at 90°. Thus, the first input coupler 11 may be coupled to the light having the first polarization from among the incident light, and the second input coupler 12 may be coupled to the light having the second polarization from among the incident light. For example, the first input coupler 11 may be coupled to the light having a P polarization, and the second input coupler 12 may be coupled to the light having an S polarization.

The first input coupler 11 and the second input coupler 12 may partially overlap each other. For example, edge regions of the first input coupler 11 and the second input coupler 12 may overlap each other, and the remaining regions thereof may not overlap each other.

In FIGS. 1A and 1B, the first input coupler 11 and the second input coupler 12 have the same lengths. However, exemplary embodiments are not limited thereto. The first input coupler 11 and the second input coupler 12 may have different lengths from each other.

The output coupler 20 may include a plurality of optical scatterers 21. Each optical scatterer 21 may include at least one selected from, for example, a slit, a slot, a spherical element, and a rod-type element. FIG. 1 illustrates a case in which a plurality of slits or slots are disposed. However, a detailed structure of each optical scatterer 21 is not limited to the slit, the slot, the spherical element, and the rod-type element and modifications may be made in various ways.

A scale (e.g., a width or a size) of each optical scatterer 21 may be a nanoscale size or a microscale size. The term "nanoscale size" used herein may refer to a size ranging from, for example, about 1 nanometers (nm) to hundreds of nm, and the term "microscale size" used herein may refer to a size ranging from, for example, about 1 micrometer (µm) to hundreds of µm. Also, the plurality of optical scatterers 21 may have random sizes and shapes, that is, non-uniform sizes and shapes. Also, when the output coupler 20 has at least one opening or groove, a material may be filled in the at least one opening or groove. The material may be different from a material (e.g., a metal) of a layer structure 110.

The authentication structure 100 may include a layer structure 110 that is a single-layer or multi-layer structure. FIG. 1 illustrates a case in which the layer structure 110 is a single-layer structure. The layer structure 110 may be one metal film (or one metal slab). The layer structure 110 may have a thickness ranging from, for example, several nanometers (nm) to several millimeters (mm), or a thickness ranging from, for example, tens of nm to hundreds of nm. When the layer structure 110 is a metal, an air layer that contacts the layer structure 110 may function as a dielectric layer. In some exemplary embodiments, a protective layer formed of a dielectric material may be further disposed on the layer structure 110.

The first and second input couplers 11 and 12 may be provided in a first area of the layer structure 110 and the output coupler 20 may be provided in a second area of the layer structure 110. The first area and the second area may be spaced apart from each other in an in-plane direction of the layer structure 110, for example, in an X-axis direction of FIG. 1. In other words, the input coupler 10 and the output coupler 20 may be horizontally spaced apart from each other.

In the present exemplary embodiment, the authentication structure 100 may be disposed on a substrate 120. The substrate 120 may be a transparent substrate such as a glass or sapphire substrate, or may be a semi-transparent or opaque substrate. The substrate 120 may be considered a part of the authentication structure 100. That is, the authentication structure 100 may include the substrate 120 and the layer structure 110. However, without the substrate 120, the layer structure 110, that is, the authentication structure 100, may be disposed directly on the object. In other words, the substrate 120 of FIG. 1B may be replaced by the object.

When the incident light L is emitted to the input coupler 10, the surface plasmons P may be generated from light coupled to the input coupler 10 on a surface of the layer structure 110 and may be transmitted to the output coupler 20. The incident light L may be coherent light and the surface plasmons P may be coherent waves. The surface plasmons P transmitted from the input coupler 10 to the output coupler 20 may be coupled to the output coupler 20 and thus converted into coherent electromagnetic waves and may be emitted to the outside of the layer structure 110. In this case, when the output coupler 20 includes a scatterer having a nanoscale size to a microscale size, the coherent electromagnetic waves may produce the speckle pattern S. The optical scatterers 21 of the output coupler 20 may have a physical unclonable function (PUF), and the speckle pattern S may have a unique identity. Accordingly, the authentication structure 100 may be used to authenticate the object, in a manner analogous to a human fingerprint.

In particular, each optical scatterer 21 of the output coupler 20 may react to different degrees according to the characteristics of the surface plasmons P due to the locations, the sizes, and an arrangement of the optical scatterers 21. Accordingly, the output coupler 20 may output different speckle patterns according to the characteristics of the surface plasmons P.

Figure 2A:
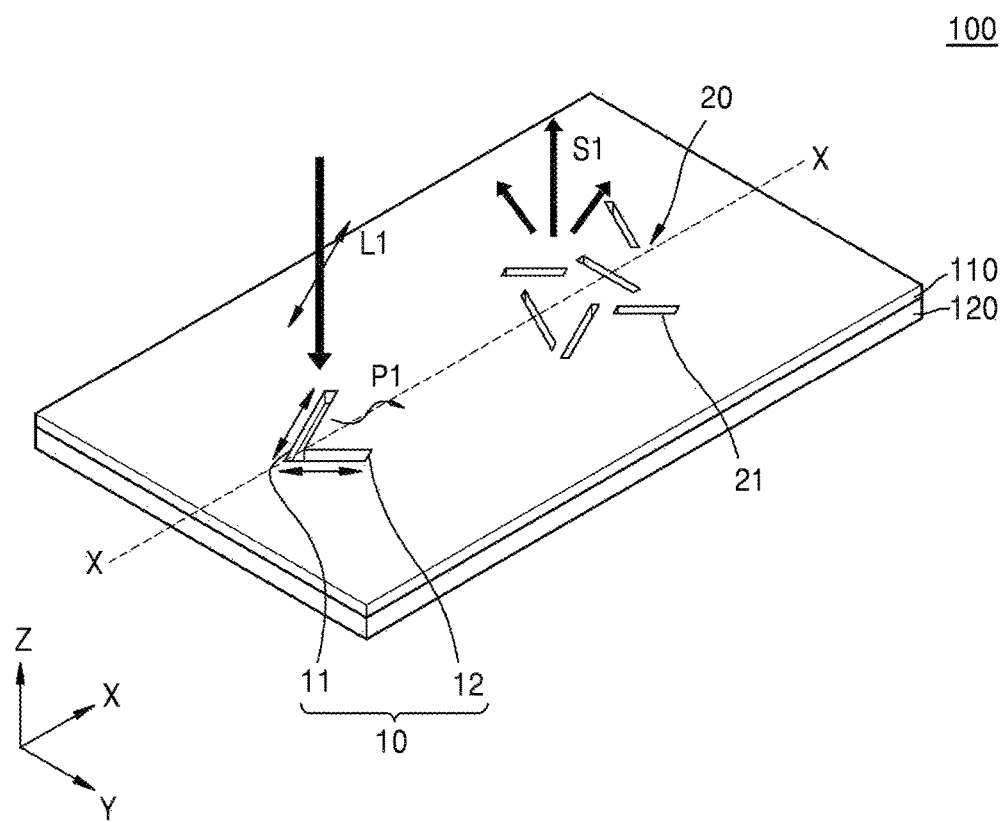
FIGS. 2A, 2B, and 2C are perspective views for explaining an authentication structure that outputs different speckle patterns according to different polarization characteristics.
Figure 2B:
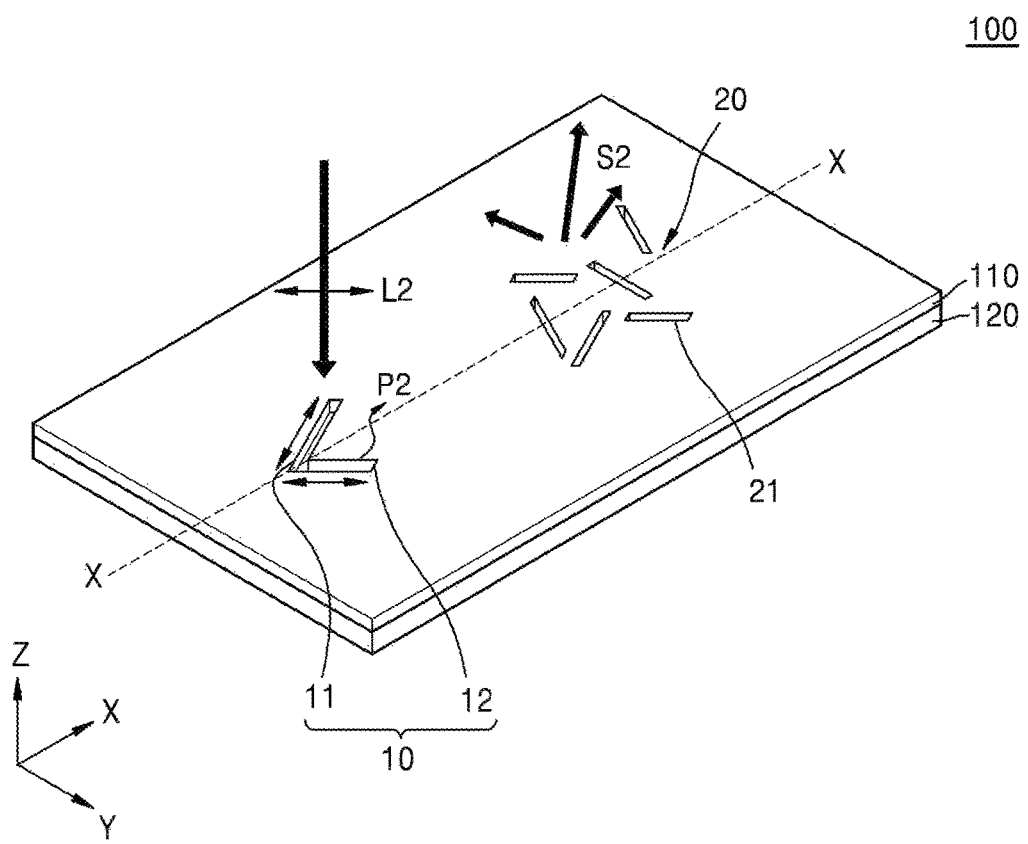
Figure 2C:
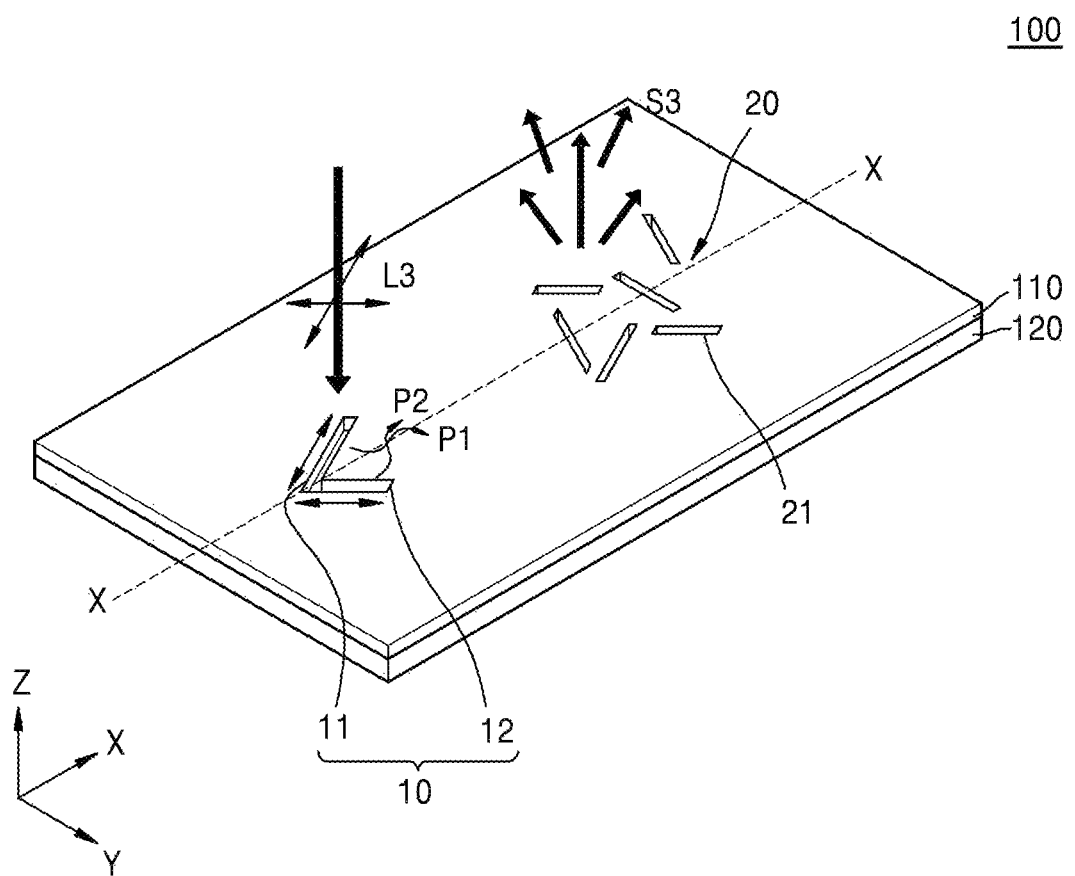

FIGS. 2A-2C are perspective views for explaining the authentication structure 100 outputting different speckle patterns according to different polarization characteristics.

First, referring to FIG. 2A, the first light L1 having first polarization characteristics may be incident to the input coupler 10. The first polarization may be a direction parallel to the first direction d1. The first input coupler 11 may generate the first surface plasmons P1 due to the first light L1, whereas the second input coupler 12 may generate no surface plasmons by not being coupled to the first light L1. The first surface plasmons P1 may be transmitted to the output coupler 20, and optical scatterers 21 of the output coupler 20 that respond to the first surface plasmons P1 may output coherent electromagnetic waves. Thus, the output coupler 20 may output a first speckle pattern S1.

Alternatively, referring to FIG. 2B, the first light L2 having second polarization characteristics may be incident on the input coupler 10. The second polarization may be a direction parallel to the second direction d2. The first input coupler 11 may be not coupled to the second light L2, whereas the second input coupler 12 may generate the second surface plasmons P2 by being coupled to the second light L2. The second surface plasmons P2 may be transmitted to the output coupler 20, and optical scatterers 21 of the output coupler 20 that respond to the second surface plasmons P2 may output coherent electromagnetic waves. Thus, the output coupler 20 may output a second speckle pattern S2.

Alternatively, referring to FIG. 2C, in response to third light L3 having the first and second polarization characteristics, the first input coupler 11 may be coupled to light having the first polarization from among the third light L3 and thus generate the first surface plasmons P1, whereas the second input coupler 12 may be coupled to light having the second polarization from among the third light L3 and thus generate the second surface plasmons P2. The first and second surface plasmons P1 and P2 may be transmitted to the output coupler 20, and the optical scatterers 21 of the output coupler 20 that respond to the first surface plasmons P1 may output electromagnetic waves and the optical scatterers 21 of the output coupler 20 that respond to the second surface plasmons P2 may output electromagnetic waves. Thus, the output coupler 20 may output a third speckle pattern S3.

As such, the authentication structure 100 may output different speckle patterns according to different polarization characteristics.

Figure 3:
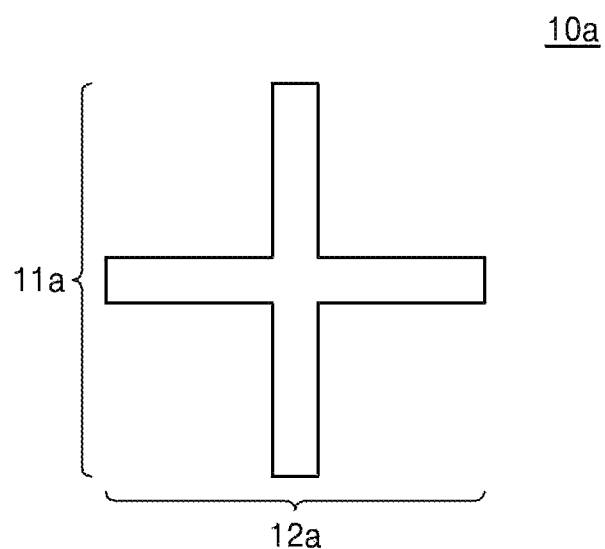
FIGS. 3-5 illustrate various input couplers according to various exemplary embodiments.
Figure 4:
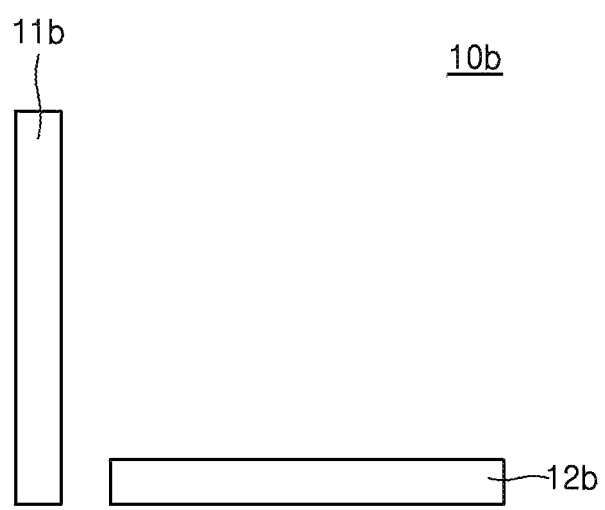
Figure 5:
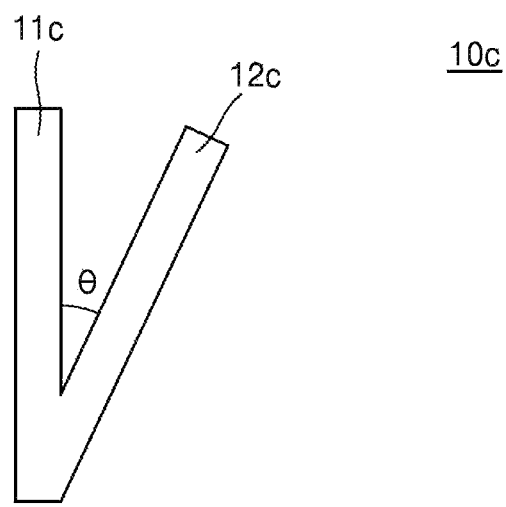

FIGS. 3-5 illustrate various input couplers 10a-10c that are applicable to the authentication structure 100 according to an exemplary embodiment.

Referring to FIG. 3, respective center regions of a first input coupler 11a and a second input coupler 12a may overlap each other, and respective edge regions thereof may not overlap each other. Even when the respective center regions of the first and second input couplers 11a and 12a overlap each other, the first input coupler 11a and the second input coupler 12a may be oriented in different directions.

Alternatively, referring to FIG. 4, a first input coupler 11b and a second input coupler 12b may be spaced apart from each other. In other words, all of the respective regions of the first input coupler 11b and the second input coupler 12b do not overlap each other. Alternatively, referring to FIG. 5, an included angle θ between the orientations of a first input coupler 11c and a second input coupler 12c may be an acute angle which is less than 90°. Alternatively, although not shown in FIG. 5, the included angle θ between the first input coupler 11c and the second input coupler 12c may be an obtuse angle which is between 90° and 180°.

Figure 6:
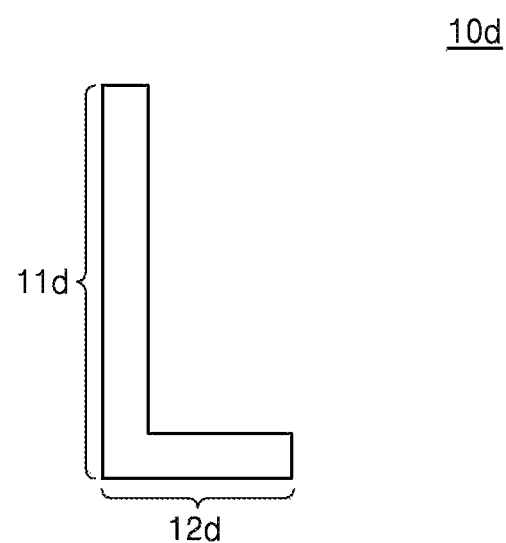
FIG. 6 illustrates an input coupler according to another exemplary embodiment.

FIG. 6 illustrates an input coupler 10d according to another exemplary embodiment.

Referring to FIG. 6, a first input coupler 11d and a second input coupler 12d may have different lengths. Accordingly, the first and second input couplers 11d and 12d may be smoothly coupled to lights having different wavelengths. When wavelengths that are coupled are different, generated surface plasmons may have different wave numbers, and the optical scatterers 21 may react to different degrees according to the different wave numbers of the surface plasmons. Thus, different speckle patterns S may be output according to different wavelengths. For example, when light in the first wavelength band is incident upon the authentication structure 100, a fourth speckle pattern may be output. When light in the second wavelength band is incident upon the authentication structure 100, a fifth speckle pattern may be output. When light in the first and second wavelength bands is incident upon the authentication structure 100, a sixth speckle pattern may be output.

Although the input coupler 10 includes two sub input couplers in FIGS. 1A, 1B, 2A-2C, and 3-6, exemplary embodiments are not limited thereto. The input coupler 10 may include three or more sub input couplers, and various orientations and various lengths may be applied to the sub input couplers. As the type of the input coupler 10 becomes diverse, various speckle patterns may become diverse. Thus, an authentication structure that outputs various speckle patterns is more unclonable than an authentication structure that outputs a single speckle pattern S. Thus, uniqueness of the authentication structure that outputs various speckle patterns increases.

Figure 7:
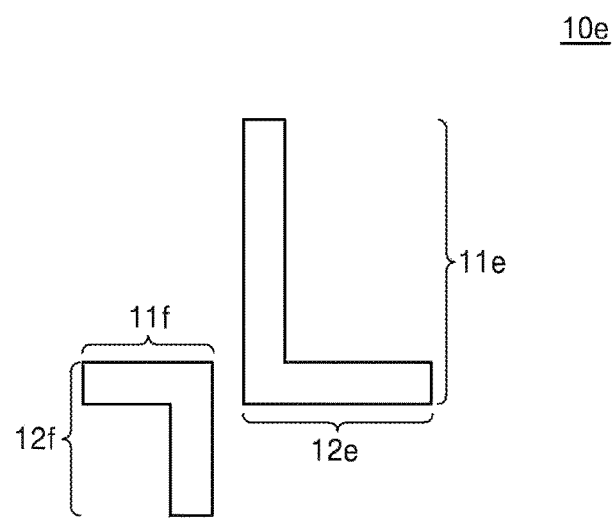
FIG. 7 illustrates an input coupler capable of responding to a plurality of light characteristics, according to an exemplary embodiment.

FIG. 7 illustrates an input coupler 10e capable of responding to a plurality of light characteristics, according to an exemplary embodiment. Referring to FIG. 7, the input coupler 10e may include a first input coupler 11e oriented in the first direction and having a first length, a second input coupler 12e oriented in the second direction and having the first length, a third input coupler 11f oriented in the first direction and having a second length, and a fourth input coupler 12f oriented in the second direction and having the second length. At least two of the first through fourth input couplers 11e, 12e, 11f, and 12f may partially overlap each other, and at least two of the first through fourth input couplers 11e, 12e, 11f, and 12f may be spaced apart from each other. As such, because the input coupler 10e is capable of being coupled to light having various light characteristics, even a single authentication structure may output various speckle patterns according to various incident light characteristics by employing the input coupler 10e. Thus, an unclonable authentication structure may be realized.

Figure 8:
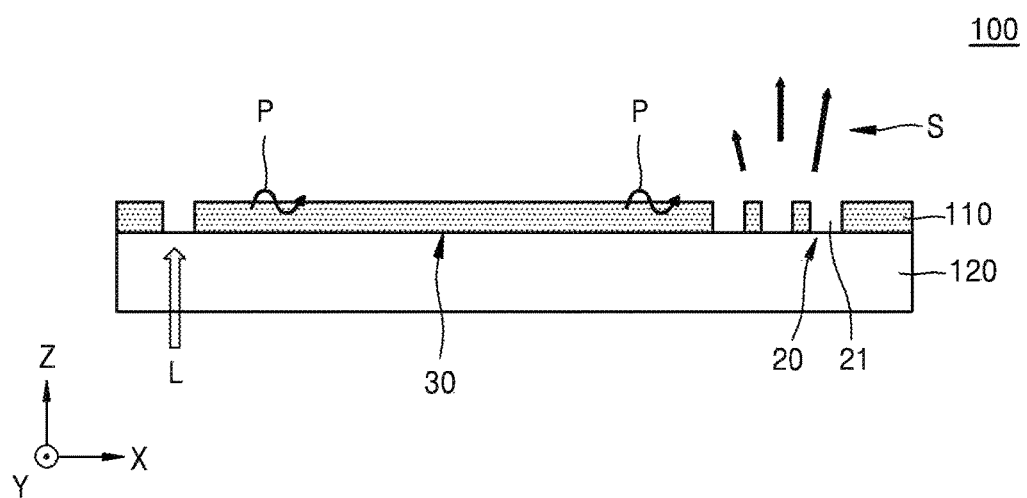
FIG. 8 is a cross-sectional view of the authentication structure of FIG. 1A, according to another exemplary embodiment.

Although the incident light L is emitted from the top of the layer structure 110 to the first and second input couplers 11 and 12 in FIGS. 1A and 1B, a direction in which the incident light L is emitted may be changed, as shown in FIG. 8. Referring to FIG. 8, the incident light L may be emitted from the bottom of the layer structure 110 to the input coupler 10. In this case, the substrate 120 may be transparent or semi-transparent to the incident light L.

FIGS. 9-12 are cross-sectional views of various authentication structures 100a-100d according to various exemplary embodiments.

Figure 9:
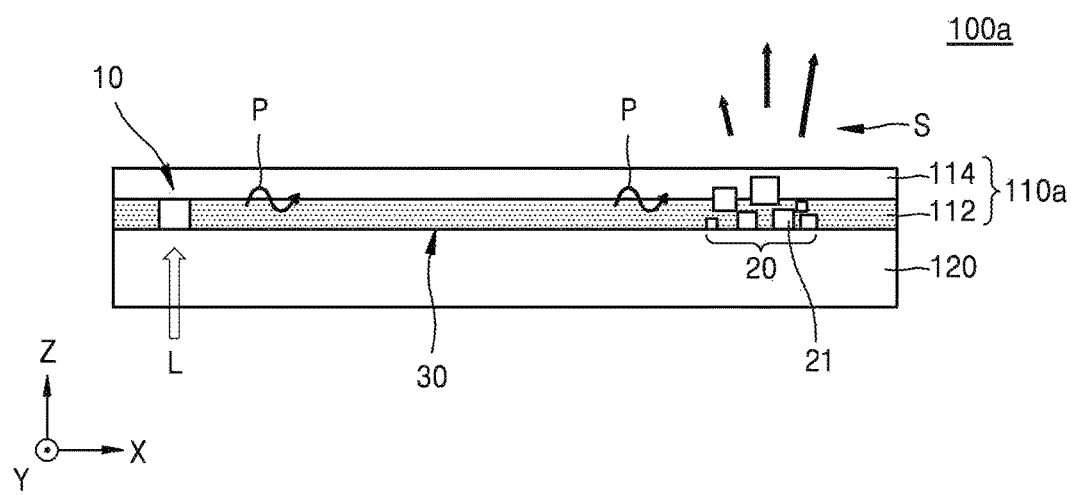
FIGS. 9-12 are cross-sectional views of various authentication structures according to various exemplary embodiments.

Referring to FIG. 9, the authentication structure 100a may include a layer structure 110a that is a multi-layer structure. The layer structure 110a may include a metal film 112 and a dielectric film 114. The dielectric film 114 may be disposed on the metal film 112. The dielectric film 114 may cover a top surface of the metal film 112, and may function as a protective film for the metal film 112. The dielectric film 114 may prevent the metal film 112 from being eroded and damaged. The dielectric film 114 may be a final layer of the authentication structure 100a.

An input coupler 10 may be provided in a first area of the layer structure 110a and an output coupler 20 may be provided in a second area of the layer structure 110a. The input coupler 10 may include, for example, a slit or a slot that is disposed in the metal film 112. Alternatively, the input coupler 10 may include a groove that extends up to a portion of the metal film 112 or one region of a substrate. The output coupler 20 may include an optical scatterer 21 that is disposed in at least one selected from the metal film 112 and the dielectric film 114. The optical scatterer 21 may have a directional shape or a symmetrical shape. A plurality of optical scatterers 21 may have non-uniform sizes and may be randomly arranged. The plurality of optical scatterers 21 may have various sizes, such as the size of an optical scatterer that penetrates through the metal film 112 and the size of an optical scatterer inserted into a portion of the metal film 112.

Because the metal film 112 and the dielectric film 114 are used in the present exemplary embodiment, the surface plasmons P may be transmitted through an interface between the metal film 112 and the dielectric film 114, thereby improving surface plasmon transmission efficiency.

Configurations of the input coupler 10 and the output coupler 20 of FIG. 9 are exemplary and various modifications may be made. For example, the input coupler 10 may be disposed in the dielectric film 114 instead of the metal film 112, or may be disposed in both the metal film 112 and the dielectric film 114. Also, when the input coupler 10 includes an opening or a groove such as a slit or a slot, a material may be filled in the opening or the groove. For example, when an opening or a groove is disposed in the metal film 112, a material (e.g., a dielectric material) having a refractive index different from that of a material of the metal film 112 may be filled in the opening or the groove. When an opening or a groove is disposed in the dielectric film 114, a material having a refractive index different from that of a material of the dielectric film 114 may be filled in the opening or the groove. The output coupler 20 may be disposed in any one selected from the metal film 112 and the dielectric film 114. Also, although the incident light L is emitted from the bottom of the layer structure 110a to the input coupler 10 in FIG. 9, the incident light L may be emitted from the top of the layer structure 110a to the input coupler 10.

Figure 10:
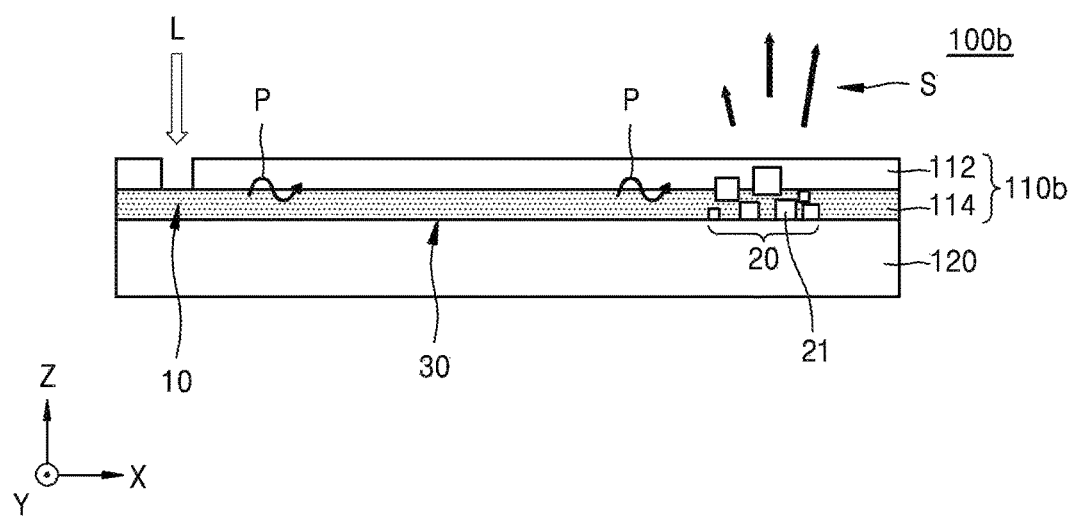

According to another exemplary embodiment, positions of the metal layer 112 and the dielectric layer 114 of FIG. 8 may be switched around, as shown in FIG. 10.

Referring to FIG. 10, the authentication structure 100b may include a layer structure 110b that is a multi-layer structure, and the layer structure 110b may include a dielectric film 114 and a metal film 112. The metal film 112 may be disposed on the dielectric film 114. An input coupler 10 may be provided in a first area of the layer structure 110b and an output coupler 20 may be provided in a second area of the layer structure 110b, and a waveguide 30 may be disposed between the input coupler 10 and the output coupler 20.

In the present exemplary embodiment, incident light L may be emitted from the top or the bottom of the layer structure 110b to the input coupler 10. FIG. 10 illustrates a case in which the incident light L is emitted from the top of the layer structure 110b. Surface plasmons P may be generated by the input coupler 10 due to the incident light L, and a speckle pattern S may be generated and output due to the surface plasmons P that are transmitted to the output coupler 20.

According to another exemplary embodiment, the layer structure 110c may include a first metal film 112a, a dielectric film 114, and a second metal film 112b. The dielectric film 114 may be disposed between the first metal film 112a and the second metal film 112b. The dielectric film 114 may be an insulating film. Accordingly, an authentication structure 100c may have a metal-insulator-metal (MIM) structure.

Figure 11:
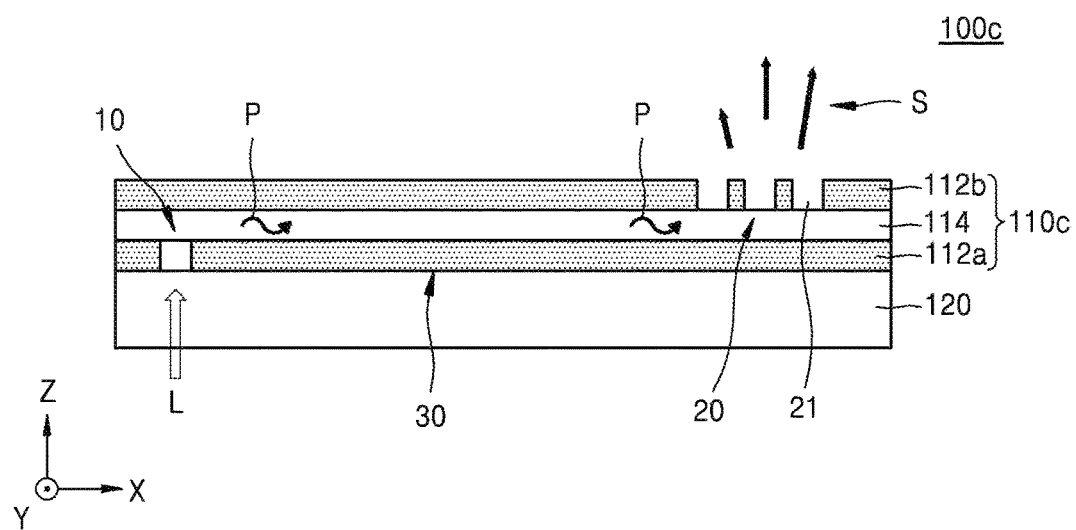

An input coupler 10 may be provided in a first area of the layer structure 110c and an output coupler 20 may be provided in a second area of the layer structure 110c. The input coupler 10 may be disposed in at least one selected from the first metal film 112a and the dielectric film 114. FIG. 11 illustrates a case in which the input coupler 10 is disposed in the first metal film 112a. The input coupler 10 may include, for example, a slit and/or a slot. A portion of the second metal film 112b corresponding to the input coupler 10 may have a continuous layer structure and may cover the top of the input coupler 10. The output coupler 20 may be disposed in at least one selected from the first metal film 112a, the dielectric film 114, and the second metal film 112b. FIG. 7 illustrates a case in which the output coupler 20 is disposed in the second metal film 112b. The output coupler 20 may include an optical scatterer 21, and the optical scatterer 21 may include, for example, a plurality of slits or slots. A portion of the layer structure 110c between the input coupler 10 and the output coupler 20 may be a waveguide 30.

When incident light L is emitted to the input coupler 10, surface plasmons P may be generated by the input coupler 10 due to the incident light L and may be transmitted to the output coupler 20 through the waveguide 30. A speckle pattern S may be generated and output by the output coupler 20 due to the surface plasmons P. Although the surface plasmons P propagate in the dielectric film 114 in FIG. 11, the surface plasmons P may actually mainly move through an interface between the first metal film 112b and the dielectric film 114 and an interface between the second metal film 112b and the dielectric film 114.

Because the second metal film 112b covers the top of the input coupler 10 in the present exemplary embodiment, the incident light L may be suppressed or prevented from being transmitted to the top of the input coupler 10 through the second metal film 112b. Accordingly, the speckle pattern S may be prevented or minimized from being affected by light transmitted to the top of the input coupler 10 through the second metal film 112b.

Figure 12:
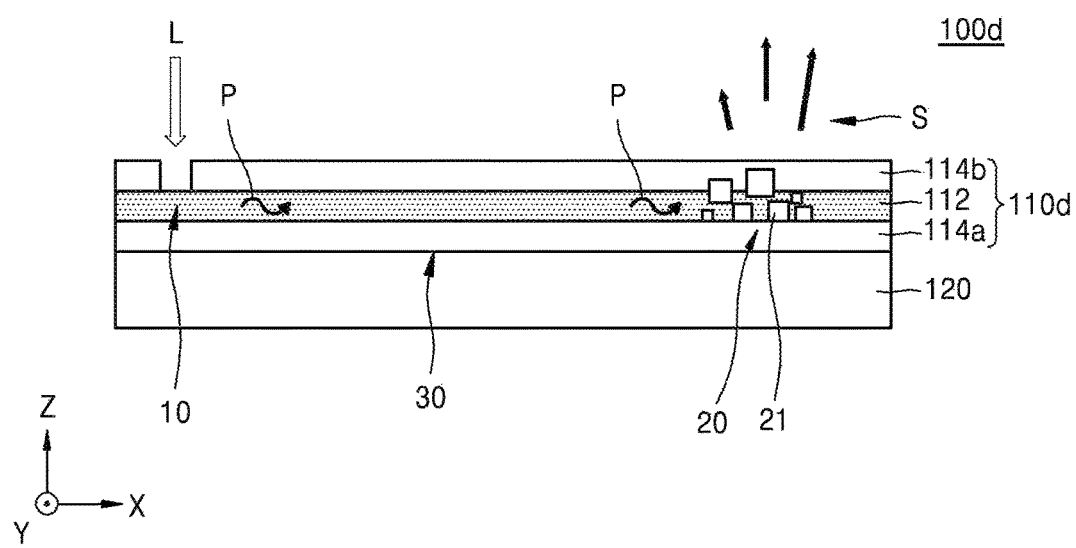

According to another exemplary embodiment, as shown in FIG. 12, the authentication structure 100d may include a layer structure 110d that is a multi-layer structure. The layer structure 110d may include a first dielectric film 114a, a metal film 112, and a second dielectric film 114b. The metal film 112 may be disposed between the first dielectric film 114a and the second dielectric film 114b. The first and second dielectric films 114a and 114b may be insulating films. Accordingly, the authentication structure 100c may have an insulator-metal-insulator (IMI) structure.

An input coupler 10 may be provided in a first area of the layer structure 110d and an output coupler 20 may be provided in a second area of the layer structure 110d. The input coupler 10 may be disposed in at least one selected from the first dielectric film 114a, the metal film 112, and the second dielectric film 114b. FIG. 12 illustrates a case in which the input coupler 10 is disposed in the second dielectric film 114b. The input coupler 10 may include, for example, a slit and/or a slot. The output coupler 20 may be disposed in at least one selected from the first dielectric film 114a, the metal film 112, and the second dielectric film 114b. FIG. 12 illustrates a case in which the output coupler 20 is disposed in the metal film 112 and the second dielectric film 114b. The output coupler 20 may include a plurality of optical scatterers 21, and each optical scatterer 21 may include at least one selected from a slit, a slot, a spherical element, and a rod-type element. FIG. 12 illustrates a case in which the plurality of optical scatterers 21 are a plurality of slits. The plurality of optical scatterers 21 may have non-uniform sizes and may be randomly arranged. A portion of the layer structure 110d between the input coupler 10 and the output coupler 20 may be a waveguide 30. Various other layer structures capable of generating surface plasmons may be applied to authentication structures.

Figure 13:
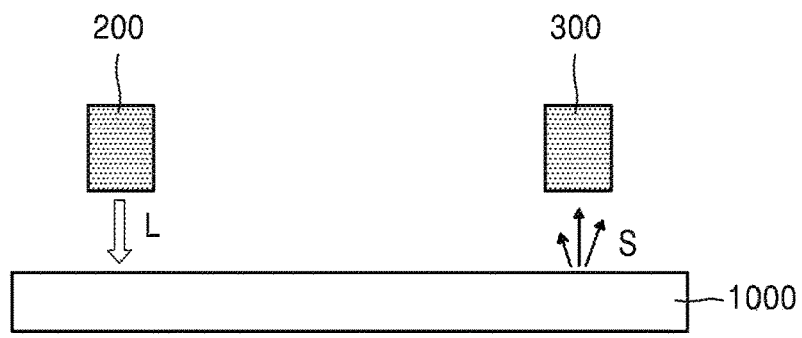
FIGS. 13 and 14 are cross-sectional views of authentication apparatuses according to exemplary embodiments.
Figure 14:
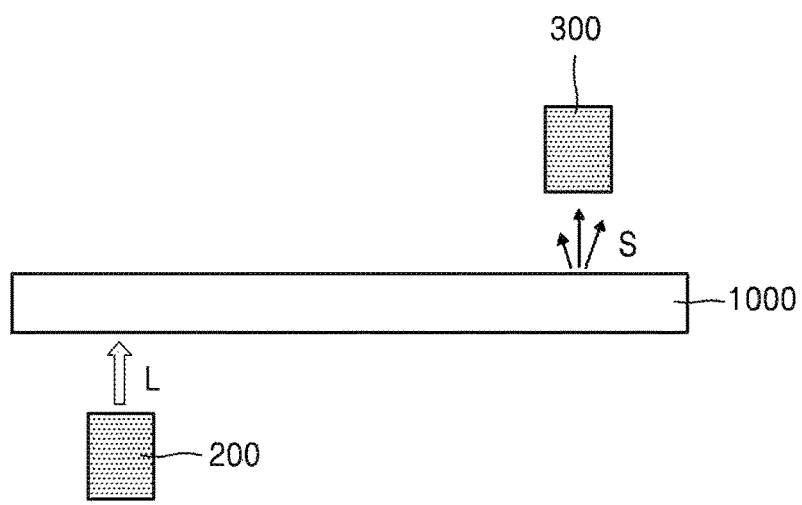

FIGS. 13 and 14 are cross-sectional views of authentication apparatuses according to exemplary embodiments.

Referring to FIG. 13, the authentication apparatus of the present exemplary embodiment may include an object 1000 which includes an authentication structure, a light source 200 that emits incident light L to an input coupler 10 of the authentication structure, and a detector 300 that detects a speckle pattern S output from an output coupler 20 of the authentication structure. Although the input coupler 10 and the output coupler 20 are not specifically shown in FIG. 13, the input coupler 10 and the output coupler 10 may have configurations that are the same as or similar to those of the input coupler 10 and the output coupler 20 of any of FIGS. 1-14.

The incident light L that is generated by the light source 200 may be coherent light and the coherent light may be laser light. In this case, the light source 200 may be a laser source. The light source 200 may be a light source capable of changing light characteristics. For example, the light source 200 may be a tunable light source capable of varying the wavelength of light, or may further include a device capable of controlling polarization of light. According to another exemplary embodiment, the light source 200 may include a plurality of sub light sources capable of light beams having different polarizations or different wavelengths. The detector 300 may include a photodiode, or may include an imaging device such as a charge-coupled device (CCD) or a complementary metal-oxide-semiconductor (CMOS) image sensor. The detector 300 may function as a camera.

In FIG. 13, the light source 200 and the detector 300 may be located in the same direction with respect to the object 1000 including the authentication structure. As shown in FIG. 13, both the light source 200 and the detector 300 may be disposed over the object 1000. However, if necessary, both the light source 200 and the detector 300 may be disposed under the object 1000.

According to another exemplary embodiment, the light source 200 and the detector 300 of an optical pickup may be located in different directions with respect to the object 1000, as shown in FIG. 14.

Referring to FIG. 14, the light source 200 may be disposed under the object and the detector 300 may be disposed over the object Alternatively, the light source 200 may be disposed over the object 1000 and the detector 300 may be disposed under the object 1000.

Also, the authentication structure according to the one or more of the exemplary embodiments may be manufactured to have a very small size. Because the input coupler and the output coupler may be disposed in a layer structure that is a single-layer or multi-layer structure by using a semiconductor device manufacturing technology, the authentication structure having a very small size may be easily manufactured. For example, the authentication structure may be manufactured to have a size less than 100 μm×100 μm or a size less than tens of μm×tens of μm, and may be manufactured to have a very small thickness. The authentication structure may be easily applied to any device requiring authentication. The authentication structure may be formed while a device or a product is manufactured, or the authentication structure may be separately manufactured and then may be attached or otherwise bonded to a device or a product. In the latter case, the authentication structure may be of a sticker type or a band type. In this regard, the authentication structure according to the one or more of the exemplary embodiments may be easily popularized or commercialized.

In addition, the authentication structure according to the one or more of the exemplary embodiments has a small size, and thus may also be applied to a flexible device. For example, the flexible device may have a local portion that is not bent and the authentication structure according to the one or more of the exemplary embodiments may be provided on the local portion.

In addition, because an optical pickup (light source or detector) corresponding to the authentication structure according to the one or more of the exemplary embodiments may also be manufactured to have a relatively small size and a technology of driving the optical pickup is relatively simple, the authentication structure may be easily authenticated by using a compact reader.

Figure 15:
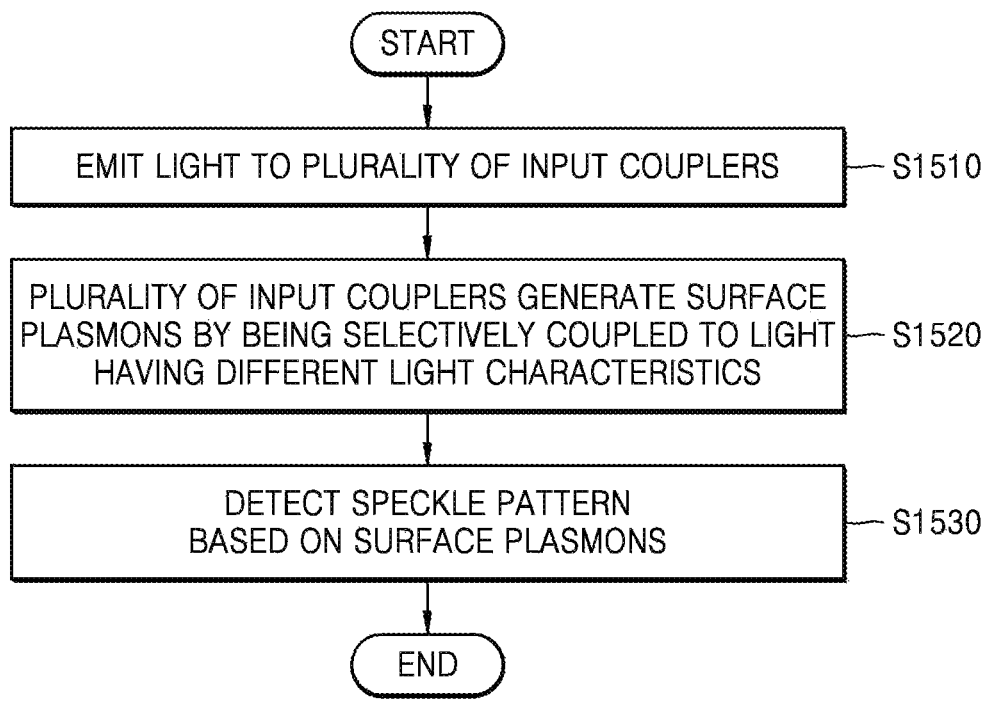
FIG. 15 is a flowchart of an authentication method according to an exemplary embodiment.

FIG. 15 is a flowchart of an authentication method according to an exemplary embodiment. The authentication method of FIG. 15 is related to the authentication structure and the apparatus or the system including the authentication structure of FIGS. 1-14. Accordingly, the authentication method of FIG. 15 may be understood based on the description of FIGS. 1-14.

Referring to FIG. 15, the authentication method of the present exemplary embodiment may include operation S1510 of emitting light to a plurality of input couplers, operation S1520 in which, because the plurality of input couplers have different geometric structures or different arrangements, the plurality of input couplers generate surface plasmons by being selectively coupled to light having different light characteristics, and operation S1530 of detecting a speckle pattern output by an output coupler based on the surface plasmons.

The authentication method may be performed by using the authentication structure and the apparatus or the system including the authentication structure of FIGS. 1-14.

Light may be emitted to the plurality of input couplers. The light may be coherent light. For example, the emitted light may be laser light. A light source may emit light having a specific light characteristic and may emit lights having different polarizations or different wavelengths according to time.

The plurality of input couplers may be coupled to light having specific light characteristics due to geometrical structures or arrangements of the plurality of input couplers and thus may generate surface plasmons. For example, when the light having the P polarization is incident, an input coupler oriented parallel to the P polarization may generate surface plasmons, whereas an input coupler oriented perpendicular to the P polarization may generate no surface plasmons.

The generated surface plasmons are transmitted to the output coupler, and the output coupler outputs a speckle pattern due to the surface plasmons. Thus, a detector may detect the output spectacle pattern. When the detected speckle pattern is a speckle pattern that is unique to the authentication structure, authentication of an object is completed. On the other hand, when the detected speckle pattern is not a speckle pattern that is unique to the authentication structure, authentication of an object is considered to be failed.

The authentication structure, the authentication method, and the apparatus using the authentication structure and the authentication method according to the one or more of the exemplary embodiments may be applied to various objects (e.g., devices, mechanism, and products) for security purposes. For example, the authentication structure, the authentication method, and the apparatus may be applied to a smart card, a memory device (e.g., a memory stick), a storage medium, or a component of an individual device. The authentication structure, the authentication method, and the apparatus may also be applied to a mobile communication device (such as a mobile phone), an Internet of Things (IOT) device, a radio-frequency identification (RFID) product or device, and a home networking system. In an apparatus or a system having openness and portability such as a mobile phone, because there are many security concerns and a software-based security technology has many limitations, a hardware-based security technology may be desirable. The authentication structure and the authentication method according to the one or more of the exemplary embodiments may be usefully applied to the hardware-based security technology. As for a mobile phone, the authentication structure and the authentication method according to the one or more of the exemplary embodiments may be used for system security, chip-level security, and data storage security purposes. Also, as for a mobile trusted module (MTM), the authentication structure and the authentication method according to the one or more of the exemplary embodiments may be used for physical security purposes. Also, the authentication structure and the authentication method according to the one or more of the exemplary embodiments may be used to verify the integrity of an individual device or a component of the individual device. The above various applications are exemplary and the authentication structure and the authentication method according to the one or more of the exemplary embodiments may be applied to any device requiring hardware-based authentication.

Authentication structures having excellent stability or reliability may be realized. Because various shapes of speckle patterns are generated according to the characteristics of incident light, unclonable authentication structures may be realized.

Because the authentication structure and the authentication method according to the one or more of the exemplary embodiments use an optical method, the authentication structure and the authentication method may be strong against various physical attacks (for example, reverse engineering, side channel attack, light emission, and fault injection). Also, because the authentication structure and the authentication method according to the one or more of the exemplary embodiments may provide a constant output by simply emitting light to an input coupler and are not greatly affected by a voltage, current, or heat, the authentication structure and the authentication method may have excellent system stability. Also, the authentication structure and the authentication method according to the one or more of the exemplary embodiments may be strong against a high output complexity and physical duplication. Also, because the authentication structure having a small size may be easily manufactured by using a general semiconductor device manufacturing technology, production costs may be reduced and the authentication structure may be easily applied to various products or devices.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An authentication structure comprising:
a first input coupler oriented in a first direction and configured to generate first surface plasmons from first light having first light characteristics from among incident light;
a second input coupler oriented in a second direction different from the first direction and configured to generate second surface plasmons from second light having second light characteristics from among the incident light; and
an output coupler spaced apart from the first and second input couplers, the output coupler comprising a plurality of optical scatterers, each of which reacting differently according to characteristics of the first and second surface plasmons due to at least one of locations, sizes, and an arrangement of the plurality of optical scatterers, and configured to output different speckle patterns based on the characteristics of the first and second surface plasmons and the plurality of the optical scatterers.

2. The authentication structure of claim 1, wherein a polarization of the first light is different from a polarization of the second light, a wavelength of the first light is different from a wavelength of the second light, or the polarization and the wavelength of the first light are different from the polarization and the wavelength of the second light.

3. The authentication structure of claim 1, wherein an included angle between the first direction and the second direction is less than 180°.

4. The authentication structure of claim 3, wherein the first direction and the second direction intersect at 90°.

5. The authentication structure of claim 1, wherein the first input coupler and the second input coupler are spaced apart from each other.

6. The authentication structure of claim 5, wherein the first input coupler and the second input coupler partially overlap each other.

7. The authentication structure of claim 1, wherein a length of the first input coupler is different from a length of the second input coupler.

8. The authentication structure of claim 1, wherein the first input coupler is coupled to light having a polarization characteristic that is parallel to the first direction.

9. The authentication structure of claim 1, wherein the first output coupler outputs a first speckle pattern based on the first surface plasmons, outputs a second speckle pattern based on the second surface plasmons, and outputs a third speckle pattern based on the first and second surface plasmons.

10. The authentication structure of claim 1, further comprising a waveguide configured to transmit at least one of the first and second surface plasmons to the output coupler.

11. The authentication structure of claim 1, wherein
the authentication structure comprises a layer structure that is a single-layer structure or a multi-layer structure,
the first and second input couplers are provided in a first area of the layer structure, and
the output coupler is provided in a second area of the layer structure.

12. The authentication structure of claim 11, wherein the first area is at a first distal end of the layer structure and the second area is at a second distal end of the layer structure.

13. The authentication structure of claim 11, wherein the first and second input couplers comprise at least one of a slit and a slot disposed in the first area of the layer structure.

14. The authentication structure of claim 11, wherein the output coupler comprises a plurality of optical scatterers disposed in the second area of the layer structure.

15. The authentication structure of claim 14, wherein each of the plurality of optical scatterers has a nanoscale size or a microscale size.

16. The authentication structure of claim 14, wherein at least one of the plurality of optical scatterers comprises a slit, a slot, a spherical element, or a rod-type element.

17. The authentication structure of claim 11, wherein the layer structure comprises a metal film.

18. A method of authenticating an authentication structure including a plurality of input couplers that have different geometric structures or arrangements from each other and an output coupler, the method comprising:

emitting light to the plurality of input couplers; and generating surface plasmons by the plurality of input couplers being selectively coupled to lights having different light characteristics among the emitted light; and detecting different speckle patterns output by the output coupler based on characteristics of the surface plasmons and a plurality of optical scatterers included in the output coupler, wherein each of the plurality of optical scatterers reacts differently according to the characteristics of the surface plasmons due to at least one of locations, sizes, and an arrangement of the plurality of optical scatterers, and wherein at least two of the plurality of input couplers are oriented in different directions from each other.

19. An authentication device comprising:

a light source configured to emit, to a layer structure, a first laser beam having a first polarization and a second laser beam having a second polarization different from the first polarization;

a first input coupler disposed on the layer structure in a first direction, the first input coupler being configured to generate first surface plasmons in response to the first laser beam being incident on the first input coupler;

a second input coupler disposed on the layer structure in a second direction different from the first direction, the second input coupler being configured to generate second surface plasmons in response to the second laser beam being incident on the second input coupler; and an output coupler disposed on the layer structure and comprising a plurality of optical scatterers, each of which reacting differently according to characteristics of the first and second surface plasmons due to at least one of locations, sizes, and an arrangement of the plurality of optical scatterers, wherein the output coupler is configured to generate a first speckle pattern in response to the first surface plasmons traveling along the layer structure and reaching the output coupler, and generate a second speckle pattern different from the first speckle pattern in response to the second surface plasmons traveling along the layer structure and reaching the output coupler, based on the characteristics of the first and second surface plasmons and the plurality of the optical scatterers.

* * * * *